(12) United States Patent
Stark

(10) Patent No.: US 6,725,084 B2
(45) Date of Patent: Apr. 20, 2004

(54) APPARATUS FOR MEASURING NONUNIFORM ATTENUATION IN A SCINTILLATION CAMERA

(75) Inventor: Iain Stark, Manotick (CA)

(73) Assignee: IS2 Research Inc., Nepean (CA)

( * ) Notice: Subject to any disclaimer, the term of this patent is extended or adjusted under 35 U.S.C. 154(b) by 387 days.

(21) Appl. No.: 09/871,832

(22) Filed: Jun. 1, 2001

(65) Prior Publication Data

US 2002/0183617 A1 Dec. 5, 2002

(51) Int. Cl.[7] .............................. A61B 5/05; A61B 6/00
(52) U.S. Cl. ........................................ 600/436; 600/407
(58) Field of Search ................................ 600/436, 407, 600/1, 2, 3, 4, 5, 6, 7, 8; 324/307, 308, 309, 310

(56) References Cited

U.S. PATENT DOCUMENTS

| | | | |
|---|---|---|---|
| 5,381,791 A | * | 1/1995 | Qian ............................ 600/436 |
| 5,595,177 A | * | 1/1997 | Mena et al. ................. 600/429 |
| 5,813,983 A | * | 9/1998 | DiFilippo et al. ........... 600/407 |
| 6,242,741 B1 | * | 6/2001 | Miller et al. ............ 250/363.02 |
| 6,484,051 B1 | * | 11/2002 | Daniel ......................... 600/436 |

\* cited by examiner

Primary Examiner—Thomas Denion
Assistant Examiner—David Robinson
(74) Attorney, Agent, or Firm—Pearne & Gordon LLP

(57) ABSTRACT

An apparatus for measuring the nonuniform attenuation caused by a patient's body in scintillation cameras is disclosed. The apparatus comprises a gantry having an annular support, a radiation source mounted on the annular support for emitting a radiation which is incident on the patients body, a dedicated radiation detector mounted on the annular support in opposed relation to the radiation source for detecting the radiation transmitted through the patient's body and a mechanism for rotating the annular support around the patient's body. The annular support defines at the center a cylindrical space where the patient's body is located along the longitudinal axis of the cylindrical space. The radiation source and radiation detector are rotated by 180 degrees around the longitudinal direction of the patients body while the radiation source scans the patient in the transversal direction such that the radiation attenuation in all directions around the patient's body can be measured.

24 Claims, 6 Drawing Sheets

APPARATUS FOR MEASURING NONUNIFORM ATTENUATION IN A SCINTILLATION CAMERA

FIELD OF THE INVENTION

The invention relates generally to a scintillation camera, and more particularly to an apparatus for measuring the non-uniform attenuation of radiation caused by a patient in the scintillation camera.

BACKGROUND OF THE INVENTION

Scintillation cameras are well known in the art of nuclear medicine, and are used for medical diagnostics. A patient ingests, or inhales or is injected with a small quantity of a radioactive isotope. The radioactive isotope emits radiations that are detected by a scintillation medium in the scintillation camera.

The scintillation medium is commonly a sodium iodide crystal, BGO or other. The scintillation medium emits a small flash or scintillation of light, in response to stimulating radiation, such as from a patient. The intensity of the scintillation of light is proportional to the energy of the stimulating radiation, such as a gamma ray. Note that the relationship between the intensity of the scintillation of light and the gamma ray is not linear.

A conventional scintillation camera such as a gamma camera includes a detector which convert into electrical signals gamma rays emitted from a patient after radioisotope has been administered to the patient. The detector includes a scintillator and an array of photomultiplier tubes. The gamma rays are directed to the scintillator which absorbs the radiation and produces, in response, a very small flash of light. The array of photodetectors, which are placed in optical communication with the scintillation crystal, convert these flashes into electrical signals which are subsequently processed. The signal processing enables the camera to produce an image of the distribution of the radioisotope within the patient.

Gamma radiation is emitted in all directions and it is necessary to collimate the radiation before the radiation impinges on the scintillation crystal. This is accomplished by a collimator which is a sheet of absorbing material, usually lead, perforated by relatively narrow channels. The collimator is detachably secured to the detector heads allowing the collimator to be changed to enable the detector head to be used with the different energies of isotope to suit particular characteristics of the patient study. The collimator may vary considerably in weight to match the isotope or study type.

Gamma rays emitted by a radioactive source, depending on its location, pass through different thicknesses and often different types of underlying or overlying tissue and therefore are attenuated by different amounts. As a result, a uniform distribution of radioactivity produces different counts at different locations of the organ, not a desirable feature in any imaging.

In conducting cardiac studies, there are usually areas of reduced radioactive readings from the patient due to self-attenuation by the body. This self-attenuation or self-absorption occurs because chest muscles tend to absorb radiation rather than emit it. Often, up to half to three quarters of the radioactivity is lost by self-absorption. In imaging the heart, areas of reduced activity in the heart muscle are seen, caused by the self-attenuation. This results in images that are inaccurate. Since the human body is generally of a non uniform shape and the heart is not centralized within the body, self-absorption must be measured. Therefore, readings are generally taken to measure or calculate how much radiation the patient absorbs in each view. These readings are then used to correct the readings from the patient activity to produce accurate images.

Known methods of measuring self absorption exist. However these methods are not reproducible in all cases. In many cases, these methods produce worse diagnostic results than without correction.

One method uses a radioactive source beamed through the patient and measures the absorption. Since the same amount of radiation will be absorbed each time, correction can be made to the created images. The problem with this method is that usually, the same detector head is used to detect the radiation from not only the patient but from the external source used to measure the attenuation. This practice reduces sensitivity and does not provide very accurate results.

Other methods require the use of an isotope of a high energy which does not provide a good measure of absorption since gamma rays emitted from high energy isotope goes through the body relatively easy and the difference between absorption and non absorption is small. Still yet, other methods use dual isotopes which is a high cost solution since these have to be replaced often.

As well, the detectors commonly include a collimator in front of it. This results in reduced sensitivity because the collimator is designed to give one to one correspondence between the emission and the detector head.

Therefore, there is a need to solve these problems and also a need for a innovative apparatus for measuring non-uniform attenuation caused by the patient's body.

SUMMARY OF THE INVENTION

According to an aspect of the present invention, there is provided an apparatus for measuring the attenuation of radiation caused by a patient's body lying in the field(s) of view of a scintillation camera. The apparatus comprises:

(a) a gantry having support, the support defining a space where the patient's body, in use, is located along a longitudinal axis defined by the space, the gantry supporting a scintillation detector head which comprises a first scintillation detector and a second scintillation detector fixed relative to each other in the form of a "V" shape;

(b) a radiation source, disposed at the apex defined by the "V" shape, for emitting radiation, the radiation being incident on the patient's body during use;

(c) a dedicated radiation detector, mounted on the support in opposed relation to the radiation source, for detecting the radiation transmitted through the patient's body;

(d) the radiation source being adapted to emit the radiation in the form of a beam which sweeps through a selected angle, and the radiation detector being adapted to move in synchronized with the sweeping motion of the beam whereby to detect the attenuation of radiation caused by the patient's body.

The radiation source comprises a radiation emitter, and an elongated casing for housing the radiation emitter. The elongated casing has a slit formed along the longitudinal axis of the casing such that the radiation can be emitted through the slit from the emitter in the form of a sheet-like beam. The radiation source includes means for rotating the elongated casing such that the radiation emitted through the slit can scan part of the patient's body in the transversal direction thereof. The radiation emitter includes an isotope emitting a radioactivity, preferably Americium 241.

The radiation detector has an elongated shape whose longitudinal axis is in parallel with the slit of the casing. The radiation detector comprises a collimator, a scintillator for converting the radiation into a light, and a photodetector for sensing the light and measuring the intensity thereof. The photodetector includes a plurality of photomultiplier tubes or a plurality of photodiodes.

The radiation detector is provided with a casing for housing the radiation detector, a track on which the radiation detector moves, and means for driving the radiation detector along the track in line with the scanning movement of the radiation.

In operation, the radiation source and radiation detector are rotated by 180 degrees around the patient's body, simultaneously while the radiation source scans the patient's body in the transversal direction thereof, such that the radiation attenuation in all directions around the patient's body can be measured.

The radiation source includes an x-ray source. The x-ray source and the radiation detector can be utilized to image the patients body while measuring the attenuation of radiation caused by the patient's body.

According to another aspect of the present invention, there is provided an apparatus for measuring the attenuation of radiation caused by a patient's body in a scintillation camera. The apparatus comprises:

(a) a gantry having an annular support ring, the annular support ring defining at the centre thereof a cylindrical space where the patient's body is located along the longitudinal axis of the cylindrical space;

(b) a radiation source, mounted on the annular support ring, for emitting a radiation, the radiation being incident on the patient's body; and (c) a dedicated radiation detector, mounted on the annular support ring in opposed relation to the radiation source, for detecting the radiation transmitted through the patient's body so that the attenuation caused by the patient's body is measured;

(d) the annular support ring being rotatable around the patient's body when in use.

Other aspects and advantages of the invention, as well as the structure and operation of various embodiments of the invention, will become apparent to those ordinarily skilled in the art upon review of the following description of the invention in conjunction with the accompanying drawings.

BRIEF DESCRIPTION OF THE DRAWINGS

Embodiments of the invention will be described with reference to the accompanying drawings, wherein.

DETAILED DESCRIPTION OF THE PREFERRED EMBODIMENT(S)

The present invention pertains to an apparatus for measuring the nonuniform attenuation of radiation caused by a patient's body in scintillation cameras. The invention will be described below, in conjunction with a scintillation camera, in which the present invention is principally utilized, but not exclusively.

Figure 1:
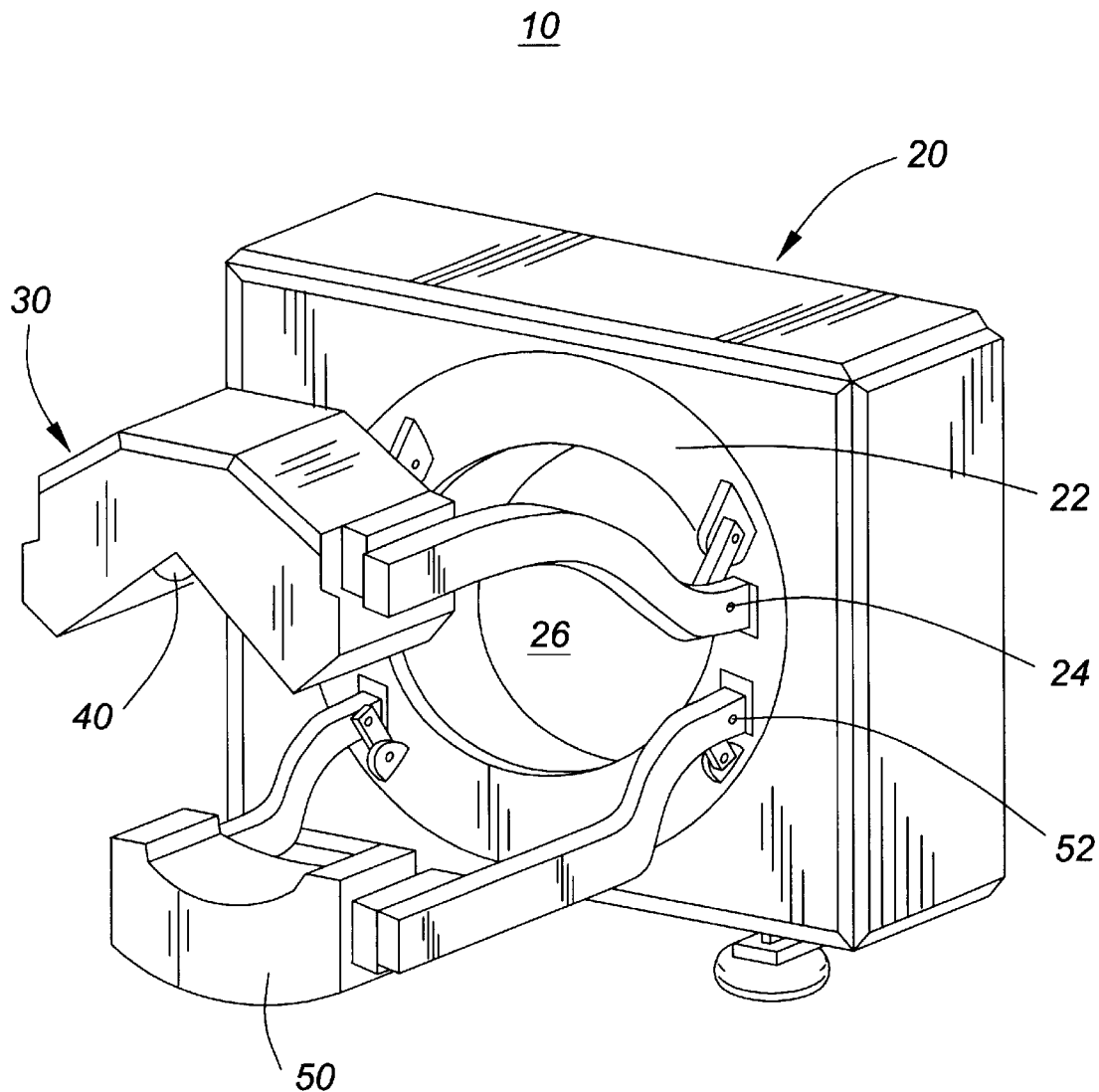
FIG. 1 is a perspective view of a scintillation camera using an apparatus according to the present invention.

FIG. 1 shows a scintillation camera, which is generally denoted by a reference numeral 10. The camera 10, in general, comprises a gantry 20 and a scintillation detector head 30 (herein after, referred to as a detector head). The gantry 20 includes a rotatable annular support 22, a mounting structure 24 for mounting the scintillation detector head 30 on the rotatable annular support 22. The annular support 22 defines at the centre thereof a cylindrical space 26, where a patient is placed for being examined. By rotating the annular support 22, the detector head 30 can be moved around the patient while the patient is positioned on a body support 61 (FIG. 2) and centred within the cylindrical space 26 along the longitudinal axis thereof, taking pictures at various angles relative to the patient. The mounting structure 24 is designed for moving the detector head 30 toward and away from the patient. Various gantry mechanisms of this type are known to those skilled in the art. For example, U.S. patent application Ser. Nos. 09/127,982 and 09/127,989, which are filed Aug. 3, 1998 by the present inventor entitled "Positioner for a scintillation camera detector head," and "Support structure for medical diagnostic equipment", respectively and has issued to U.S. Pat. No. 6,255,656 and U.S. Pat. No. 6,288,398, respectively, disclose suitable supporting and driving mechanisms for the scintillation cameras, and the disclosures of these applications are incorporated herein by reference thereto.

In the scintillation camera 10 of FIG. 1, there is shown an apparatus for measuring non-uniform attenuation caused by the patient being examined. The apparatus generally comprises a radiation source 40 and a radiation detector 50. In this embodiment, the radiation source 40 is detachably attached to the detector head 30, and the radiation detector 50 is mounted on the annular support 22 by a mounting structure 52, which can be identical to the mounting structure 22 for the detector head 30 in terms of the mechanism and the operation thereof.

Figure 2:
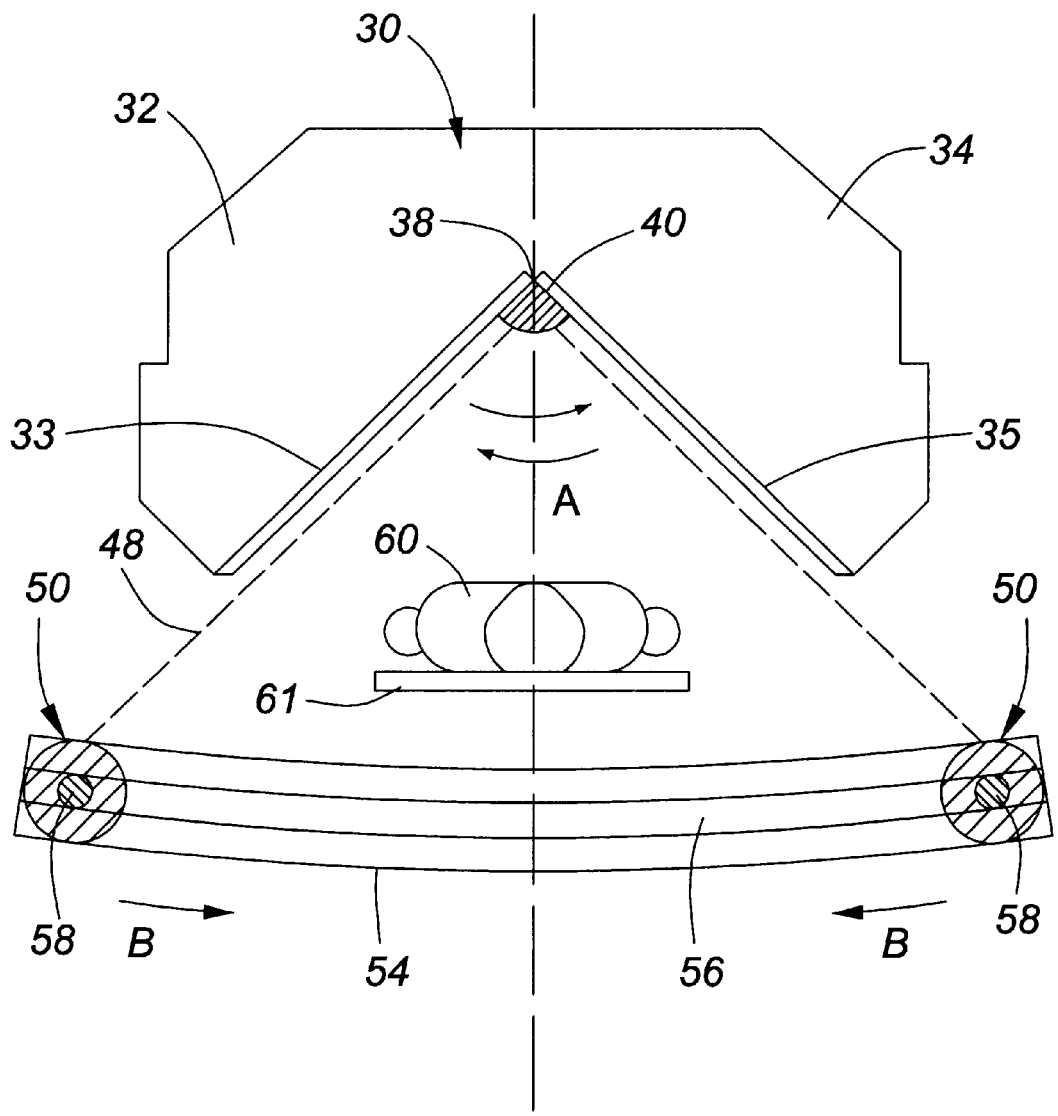
FIG. 2 is a schematic representation illustrating one embodiment of the invention.

As shown in FIG. 2, the detector head 30 is a dual detector head, which comprises a first scintillation detector head 32 and a second scintillation detector head 34. The first detector head 32 includes a scintillator (not shown), a plurality of photomultiplier tubes (not shown), and a first collimator 33, The second detector head 34 also includes a scintillator (not shown), a plurality of photomultiplier tubes (not shown), and a second collimator 35. The collimators 33 and 35 define a first camera surface (a first field of view) and a second camera surface (a second filed of view) respectively. The first and second detector heads 32 and 34 are fixed relative to each other such that the first and second camera surfaces form an inverted "V" shape, defining an apex line 38 along the meeting line between the first and second detector heads 32 and 34 In this embodiment, the first camera surface and second camera surface are substantially at 90 degrees to each other.

Referring to FIGS. 1 and 2, the geometric set-up of this embodiment will be described below. As shown in the FIGS.

1 and 2, the radiation source 40 is mounted on the dual detector head 30 and extends along the apex 38 line described above. The radiation detector 50 is mounted on the annular support 22 of the gantry 20 in opposed spaced relationship to the radiation source 40. That part of the patient's body to be examined is located between the radiation source 40 and detector 50 during use. The radiation 48 emitted by the source 40 is not detected by the detector head 30, but by the radiation detector 50 as will be more clearly described below. It is noted that the invention is not limited to the geometry shown in FIGS. 1 and 2. For example, the radiation source 40 can be mounted on a single detector head in an appropriate position thereof, which may be replaced with the dual detector head 30, or mounted on the annular support 22 in opposition to the radiation detector 50.

Figure 3:
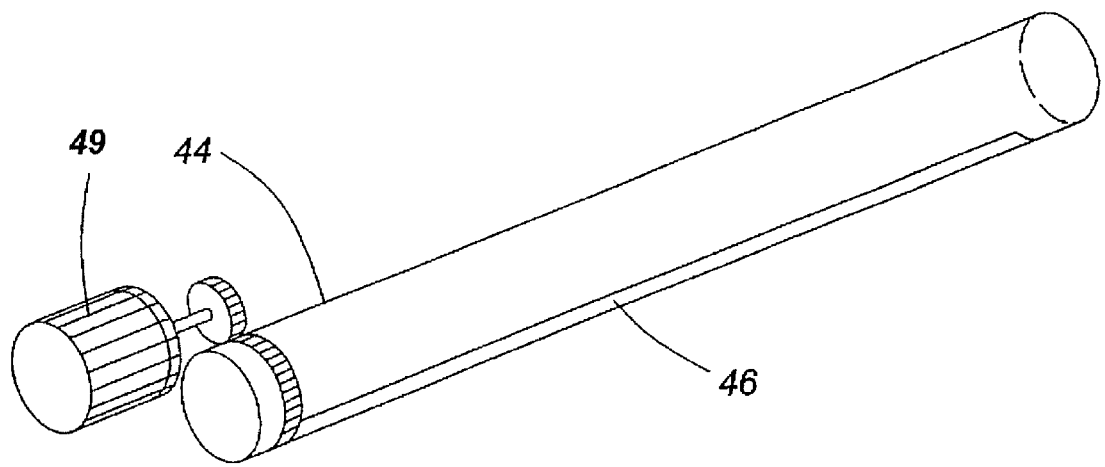
FIG. 3 is a perspective view showing the radiation emitter casing of the radiation source in FIG. 2.
Figure 4:
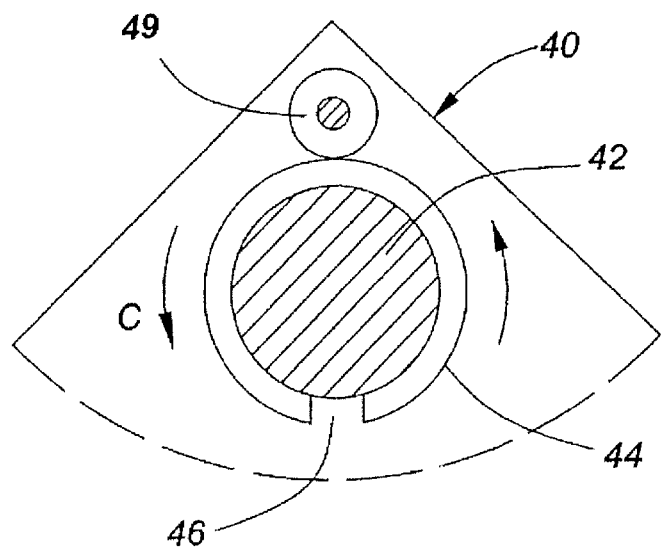
FIG. 4 is a schematic representation showing the sectional configuration of the radiation source.

FIGS. 3 and 4 illustrate the structure of the radiation source 40. According to this embodiment, the radiation source 40 has an elongated shape extending along the apex line 38 where the first and second detector heads 32 and 34 meet each other. As shown in FIGS. 3 and 4, the radiation source 40 includes a radiation emitter 42 and an elongated casing 44 for housing the radiation emitter 42. The casing 44 includes an elongated slit 46 formed along the longitudinal axis of the casing. Therefore, the radiation emitted through the slit by the radiation emitter 42 forms a sheet-like radiation beam 48 (FIG. 2), which is incident on the patient's body 60. The radiation source 40 is provided with means, such as a stepping motor 49, for rotating the casing 44 as indicated by arrow C in FIG. 4, such that the radiation beam 48 can sweep around and scan the patient's body 60 in the directions indicated by arrows A in FIG. 2. Therefore, by virtue of the scanning effected by the sheet-like radiation beam 48, a selected area of the patient's body can be scanned and examined with each sweep of the radiation beam. This structure and the advantages associated therewith will be described hereafter in greater detail, in conjunction with the explanation of the radiation detector 50.

In situations when the measurement of attenuation is not required or the procedure is finished, the lead casing 44 can be rotated by the rotating means (e.g. the stepping motor 49) in order for the slit 46 of the casing to face upward, for example, to face the apex 38 of the detector head 30, such that the patient is not unnecessarily exposed to the radioactivity from the source 40.

The elongated casing 44 in the radiation source 40 is preferably made of lead. The radiation emitter 42 is radioactive isotope, Americium 241.

Figure 2A:
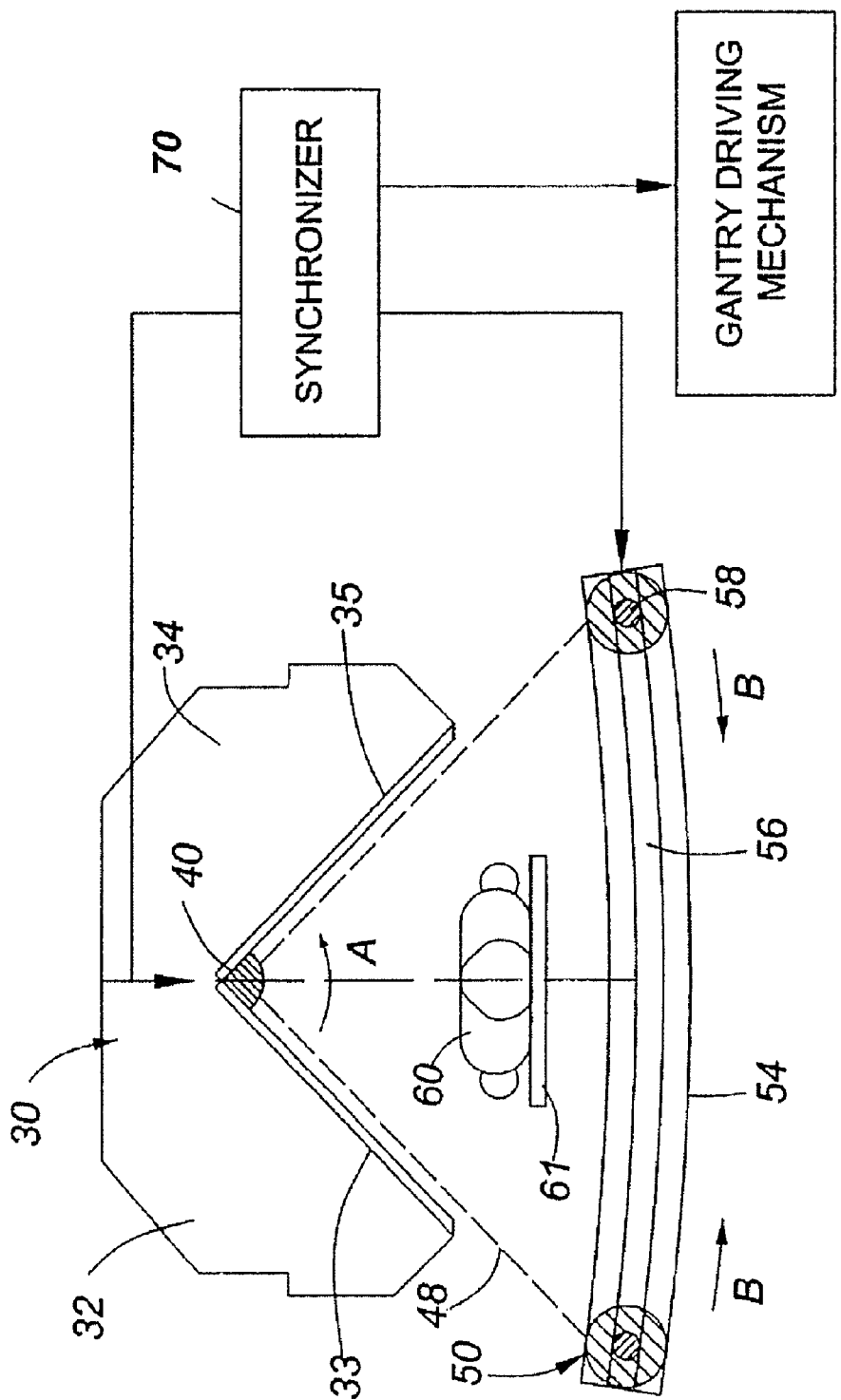
FIG. 2A is a schematic representation showing the synchronized operation of the radiation source and detector in the apparatus.

FIG. 2A is a schematic representation showing the synchronized operation of the radiation source 40 and detector 50. Referring to FIGS. 2 and 2A, the configuration and operation of the radiation detector 50 will be described below. According to this embodiment, the radiation detector 50 is provided with a track 56, and a driving means, such as a stepping motor 58, for moving the radiation detector 50 along the track 56 as indicated by an arrow B. The stepping motor 58 for moving the detector 50 is synchronized with the stepping motor 49 for rotating the lead casing 44 of the source 40 by a synchronizer 70 shown in FIG. 2A. The radiation detector 50 is also provided with a housing 54 for housing the detector 50, the track 56, and the stepping motor 58.

The radiation detector 50 also has an elongated shape correspondingly to the elongated casing 44 of the radiation source 40, such that the longitudinal axis of the radiation detector 50 remains in parallelism with the slit 46 of the radiation source 40 during the operation of the apparatus.

The radiation detector comprises a collimator, a scintillator (a scintillation crystal) for converting the radiation transmitted through the patient's body into a light, and a photodetector (a photosensor) for sensing the light and measuring the intensity thereof. This configuration of the radiation detector is well known to those skilled in the art, However, the embodiment shown has an elongated shape as noted above, and therefore, the collimator and the scintillator have an elongated form. Also, the photodetector can include a plurality of photomultiplier tubes arranged along the longitudinal axis of the elongated radiation detector 50. Alternatively, the photodetector can be a plurality of photodiodes, also arranged in the longitudinal direction of the detector 50.

Referring to FIGS. 1 to 5, the operation of the apparatus is described below. The sheet-like radiation beam 48 emitted through the slit 46 is incident on and scans the patient's body 60 in the transversal direction thereof indicated by an arrow A by rotating the casing 44 of the radiation source 40, by means of the stepping motor 49. Simultaneously, the radiation detector 50 (driven in synchronism with the casing 44) follows the scanning movement of the radiation beam 48, as indicated by an arrow B, such that the detector 50 can sense and measure the intensity of the radiation transmitted through the patient's body 60 during the scanning by the radiation beam. Further, a large area of the patient's body 60 can be scanned at a time by the sheet-like beam 48. The radiation incident on the body experiences attenuation by self-absorption and scattering by the patient's organs and the tissues surrounding them. The radiation transmitted through the body will be detected and measured by the radiation detector 50 placed on the opposite side of the patient 60, so that the attenuation caused by the patient's body 60 can be measured. The amount of attenuation varies depending the sizes and shapes of organs, and consequently, it varies with patients, which leads to a non-uniform distribution of attenuation.

Figure 5A:
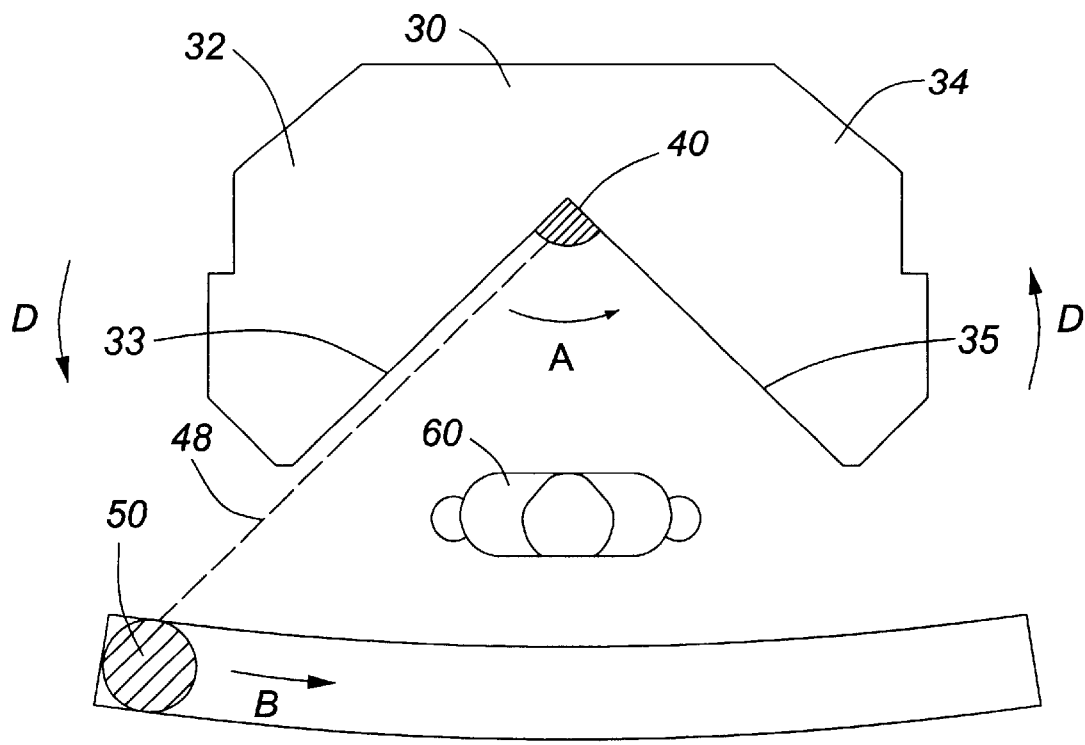
FIGS. 5A and 5B are schematic representations showing the operation of the apparatus.
Figure 5B:
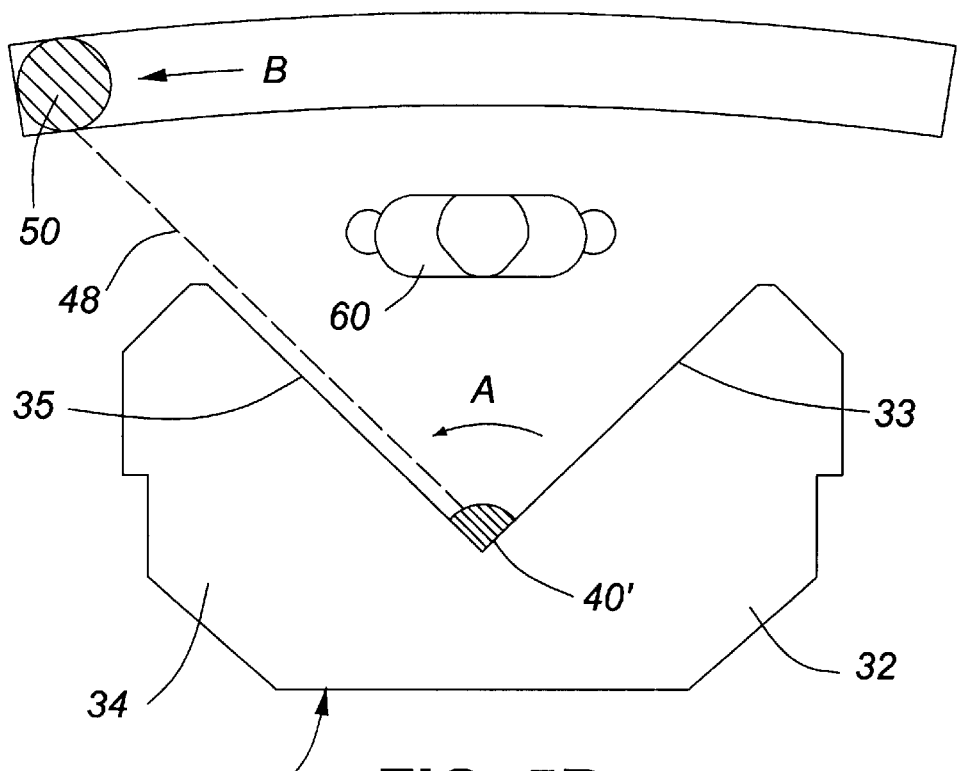

As shown in FIG. 1 and noted above, the radiation source 40 attached to the detector head 30 can rotate around the patient 60 together with the detector head by effecting the rotation of the annular support 22 of the gantry 20. At the same time, the radiation detector 50 rotates around the patient, while remaining in opposed spaced relation to the radiation source 40. As shown in FIGS. 5A and 5B, the radiation source 40 and detector 50 are rotated together by 180 degrees around the patient's body (as indicated by an arrow D) simultaneously, while the radiation beam 48 together with the detector 50 scans the patient's body by 90 degrees, as indicated by the arrow A. As shown in FIG. 2A the 180 degree-rotation of the source and detector is also synchronized with the 90 degree-scanning thereof by means of the synchronizer 70. In this way, the non-uniform attenuation associated with all directions around the patient's body 60 can be measured in a single operation with respect to a desired part of the body. Consequently, with the combination of the scanning effected by the sheet-like radiation beam coupled with the rotation of the radiation source and detector, non-uniform attenuation distribution with respect to a certain selected area or part of patient's body can be measured in a single operation, without any necessity of multiple scanning and rotation as in prior art equipment.

Figure 6:
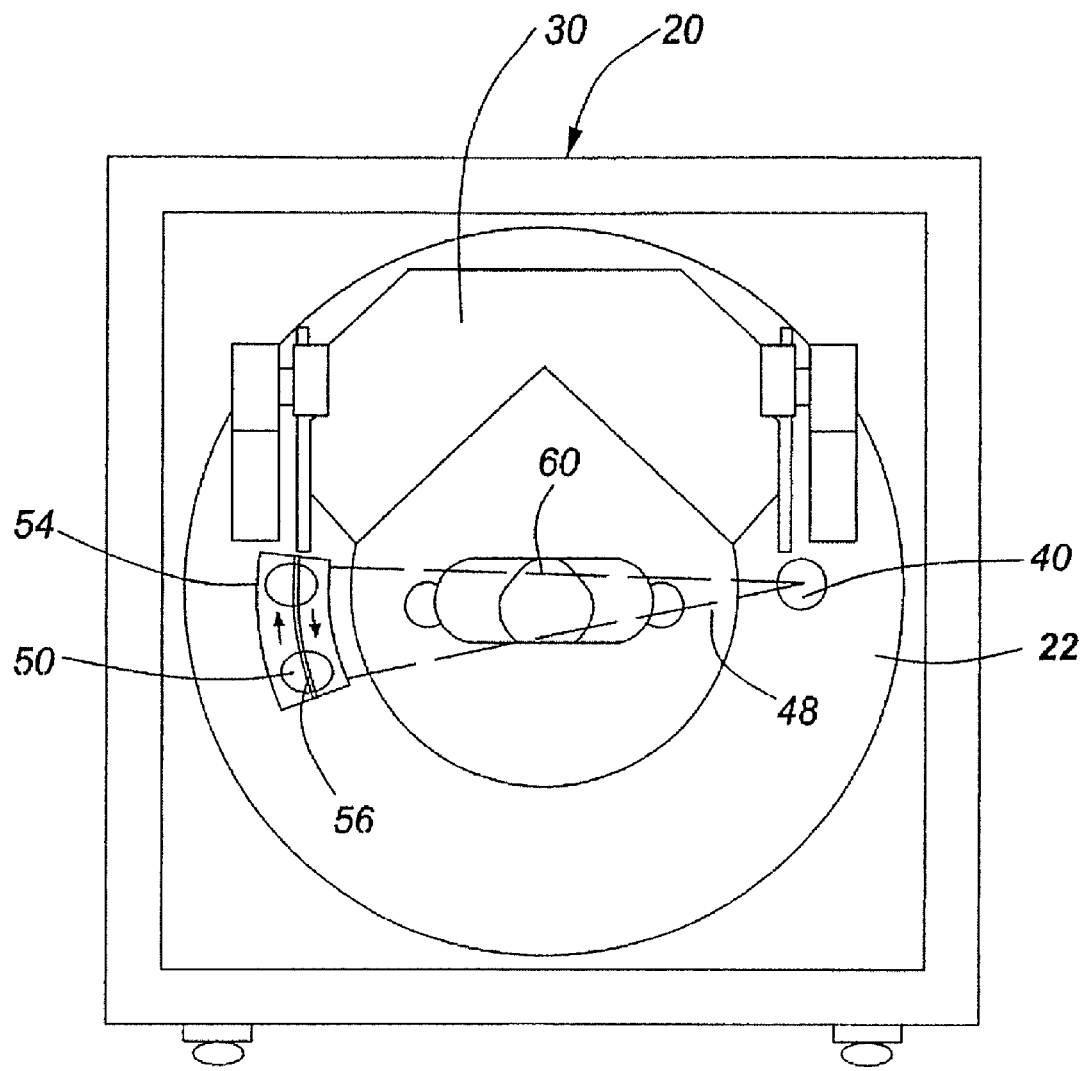
FIG. 6 is a schematic illustration of another embodiment of the invention.

FIG. 6 illustrates another embodiment of the invention. In this embodiment, the radiation source 40 is secured to the annular support 22 of the gantry 20 instead of the detector head 30, and the radiation detector 50 is likewise movably mounted on the annular support 22 as in the previous embodiment. The structures of the radiation source 40 and detector 50 are identical to those of the previous embodiment. Also, the operation of the apparatus is essentially the same as in FIGS. 2, 5A and 5B, except that the angular distance of scanning by the radiation beam 48 is smaller than the previous embodiment due to the geometrical limitations of the structure relative to the camera head 30. However, as with the previous embodiment, non-uniform attenuation distribution with respect to a certain selected area or part of a patient's body can be measured in one operation without any necessity of multiple scanning and rotation as in prior art equipment, resulting from the combination of the scanning of the sheet-like radiation beam 48, and the synchronized rotation of the radiation beam from the source 40 and detector 50.

In an alternative version, the radiation source 40 can include an x-ray source. In the case that an x-ray source is utilized as a radiation source, an anatomical image of the desired body part of the patient can be obtained, simultaneously while measuring the non-uniform attenuation distribution for the same body part.

While the invention has been described according to what are presently considered to be the most practical and preferred embodiments, it must be understood that the invention is not limited to the disclosed embodiments. Those ordinarily skilled in the art will understand that various modifications and equivalent structures and functions may be made without departing from the spirit and scope of the invention as defined in the claims. Therefore, the invention as defined in the claims must be accorded the broadest possible interpretation so as to encompass all such modifications and equivalent structures and functions.

What is claimed is:

1. An apparatus for measuring the attenuation of radiation caused by a patient's body lying in the field(s) of view of a scintillation camera, the apparatus comprising:
   (a) a gantry having a support, said support defining a space where the patient's body, in use, is located along a longitudinal axis defined by said space, said gantry supporting a scintillation detector head which comprises a first scintillation detector and a second scintillation detector fixed relative to each other in the form of a "V" shape;
   (b) a radiation source, disposed at the apex defined by said "V" shape, for emitting radiation, said radiation being incident on the patient's body during use;
   (c) a dedicated radiation detector, mounted on said support in opposed relation to said radiation source, for detecting said radiation transmitted through the patient's body;
   (d) said radiation source being adapted to emit said radiation in the form of a beam which sweeps through a selected angle, and said radiation detector being adapted to move in synchronization with the sweeping motion of said beam whereby to detect the attenuation of radiation caused by the patient's body.

2. An apparatus according to claim 1, wherein said support includes an annular support, said annular support defining a cylindrical space where the patient's body is positioned along the longitudinal axis of said cylindrical space, and said annular being rotatable about the longitudinal axis of said cylindrical space.

3. An apparatus according to claim 1, wherein said radiation source comprises:
   (a) a radiation emitter;
   (b) an elongated casing for housing said radiation emitter, said elongated casing having a slit formed along the longitudinal axis of said casing, such that the radiation can be emitted through said slit from said emitter in the form of a sheet-like beam; and
   (c) means for rotating said elongated casing such that said radiation emitted through said slit can scan part of the patient's body in the transversal direction thereof.

4. An apparatus according to claim 3, wherein said radiation detector is mounted on said support for movement therealong in synchronization with the rotation of said casing whereby said sheet-like beam can be detected by the detector as said casing is rotated.

5. An apparatus according to claim 3, wherein said radiation emitter includes an isotope emitting a radioactivity, namely Americium 241.

6. An apparatus according to claim 4, wherein said radiation detector has an elongated shape whose longitudinal axis is in parallelism with the slit of said casing.

7. An apparatus according to claim 6, wherein said radiation detector is provided with:
   (a) a casing for housing said radiation detector;
   (b) a track on which said radiation detector moves; and
   (c) means for driving said radiation detector along said track in synchronization with the scanning movement of said sheet-like radiation beam.

8. An apparatus according to claim 7, wherein said support is adapted to permit said radiation source and radiation detector to be rotated by a selected degrees around the patient's body while said radiation source scans the patient's body in the transversal direction thereof, such that the radiation attenuation in all directions around the patient's body can be measured.

9. An apparatus according to claim 6, wherein said radiation detector comprises:
   (a) a collimator
   (b) a scintillator for converting said radiation into a light; and
   (c) a photodetector for sensing said light and measuring the intensity thereof.

10. An apparatus according to claim 9, wherein said photodetector includes a plurality of photomultiplier tubes.

11. An apparatus according to claim 9, wherein said photodetector includes a plurality of photodiodes.

12. An apparatus according to claim 1, wherein said radiation source includes an x-ray source.

13. An apparatus according to claim 12, wherein said x-ray source and said radiation detector are utilized to image said patient while measuring the attenuation of said radiation caused by said patient's body.

14. An apparatus for measuring the attenuation of radiation caused by a patient's body in a scintillation camera, the apparatus comprising:
   (a) a gantry having an annular support ring, said annular support ring defining at the centre thereof a cylindrical space where the patient's body is located along the longitudinal axis of said cylindrical space;
   (b) a radiation source, mounted on said annular support ring, for emitting a radiation, said radiation being incident on the patient's body; and
   (c) a dedicated radiation detector, mounted on said annular support ring in opposed relation to said radiation source, for detecting said radiation transmitted through the patient's body so that the attenuation caused by the patient's body is measured;
   (d) said annular support ring being rotatable around the patient's body when in use.

15. An apparatus according to claim 14, wherein said radiation source comprises:

(a) a radiation emitter;

(b) an elongated casing for housing said radiation emitter, said elongated casing having a slit formed along the longitudinal axis of said casing, such that the radiation can be emitted through said slit from said emitter in the form of a sheet-like beam; and (c) means for rotating said elongated casing such that said radiation emitted through said slit can scan part of the patient's body in the transversal direction.

16. An apparatus according to claim 15, wherein said radiation emitter includes an isotope emitting a radioactivity, namely Americium 241.

17. An apparatus according to claim 15, wherein said radiation detector has an elongated shape whose longitudinal axis is in parallelism with the slit of said casing.

18. An apparatus according to claim 15, wherein said radiation detector is provided with:

(a) a casing for housing said radiation detector;

(b) a track on which said radiation detector moves; and (c) means for driving said radiation detector along said track in synchronization with the scanning movement of said radiation.

19. An apparatus according to claim 16, wherein said annular support ring is adapted to permit said radiation source and radiation detector to be rotated by a selected degrees around the longitudinal direction of the patient's body while said radiation source scans said patient in the transversal direction of the patient's body, such that the radiation attenuation in all directions around said patient can be measured.

20. An apparatus according to claim 17, wherein said radiation detector comprises:

(a) a collimator;

(b) a scintillator for converting said radiation into a fight; and (c) a photodetector for sensing said light and measuring the intensity thereof.

21. An apparatus according to claim 20, wherein said photodetector includes a plurality of photomultiplier tubes.

22. An apparatus according to claim 20, wherein said photodetector includes a plurality of photodiodes.

23. An apparatus according to claim 14, wherein said radiation source includes an x-ray source.

24. An apparatus according to claim 23, wherein said x-ray source and said radiation detector are utilized to image said patient while measuring the attenuation of said radiation caused by said patient's body.

* * * * *